United States Patent [19]

Bauman

[11] 4,166,073
[45] Aug. 28, 1979

[54] UNSYMMETRICAL OLIGOQUATERNARY AMMONIUM COMPOUNDS

[75] Inventor: Robert A. Bauman, New Brunswick, N.J.

[73] Assignee: Colgate Palmolive Company, New York, N.Y.

[21] Appl. No.: 826,587

[22] Filed: Aug. 22, 1977

Related U.S. Application Data

[60] Division of Ser. No. 82,626, Oct. 21, 1970, abandoned, which is a continuation-in-part of Ser. No. 716,412, Mar. 27, 1968, abandoned.

[51] Int. Cl.² .......................... C07C 87/30; A01N 9/20
[52] U.S. Cl. .............................. 260/567.6 P; 424/329; 424/54
[58] Field of Search .................. 260/567.6 P; 424/329

[56] References Cited

U.S. PATENT DOCUMENTS

| | | | |
|---|---|---|---|
| 2,113,606 | 4/1938 | Taub et al. | 260/567.6 P |
| 2,654,785 | 10/1953 | Mieschen et al. | 260/567.6 P |
| 3,055,939 | 9/1962 | Cavallito et al. | 260/567.6 P |
| 3,079,439 | 2/1963 | Hwa | 260/567.6 P |
| 3,489,663 | 1/1970 | Bayer et al. | 260/567.6 R |
| 3,493,615 | 2/1970 | Bauman | 260/567.6 P |
| 3,925,556 | 12/1975 | Bauman | 260/567.6 P |

*Primary Examiner*—James H. Reamer
*Attorney, Agent, or Firm*—Robert L. Stone; Murray M. Grill; Herbert S. Sylvester

[57] ABSTRACT

Unsymmetrical oligoquaternary ammonium compounds containing at least two onium nitrogen atoms. Typical compounds are:

$[C_{12}H_{25}N^+(Me)_2(CH_2)_4N^+(Me)_2CH_2C_6H_5]Br$;
$[C_{14}H_{29}N^+(Me)_2(CH_2)_{10}N^+(Me)_2CH_2C_6H_4Cl]Br_2$ and
$[C_{12}H_{25}N^+(Me)_2(CH_2)_4N^+(Me)_2(CH_2)_2N^+(Me)_2CH_2C_6H_5]Br_3$ These compounds are effective as antimicrobial agents and as anticaries agents.

7 Claims, No Drawings

UNSYMMETRICAL OLIGOQUATERNARY AMMONIUM COMPOUNDS

This application is a divisional of application Ser. No. 82,626, filed Oct. 21, 1970, now abandoned, which is a Continuation-In-Part of Ser. No. 716,412, filed Mar. 27, 1968, now abandoned.

The present invention relates to unsymmetrical oligoquaternary ammonium compounds and, more particularly, to unsymmetrical oligoquaternary ammonium compounds containing at least two onium nitrogen atoms, having anti-microbial activity, having anti-caries properties and having novel adsorption and desorption properties.

In recent years a multitude of quaternary ammonium compounds having antifungal and antibacterial capabilities have been disclosed. These quaternary ammonium compounds may be divided into two major groups (A) those quaternaries having only one onium nitrogen atom and (B) those quaternaries having more than one onium nitrogen atom. The latter group can be subdivided into bisquaternaries having two onium nitrogen atoms and tri and higher quaternaries having three or more onium nitrogen atoms. Each of these subdivisions of the poly-onium nitrogen atom quaternaries can be further divided into the symmetrical and the unsymmetrical poly-onium nitrogen atom quaternaries dependent upon the substituent groups attached to the terminal onium nitrogen atoms of the poly-onium nitrogen atom quaternaries. Thus, when all of the substituent groups attached to each terminal onium nitrogen atom are the same, the quaternary is considered to be symmetrical. When one or more of the substituent groups attached to one terminal onium nitrogen atom of a poly-onium nitrogen atom quaternary is or are different from the constituent groups attached to the other terminal onium nitrogen atom the quaternary is considered to be unsymmetrical or asymmetrical.

Those skilled in the art will recognize that prior art descriptions of poly-onium compounds do not indicate that the efficacy is dependent upon the number of $CH_2$-groups which separate the two onium-nitrogen atoms in the bis-quaternaries or that in the poly-onium compounds having three onium-nitrogen atoms that the efficacy is dependent upon the number of $CH_2$-groups separating from the central onium-nitrogen atom the terminal onium-nitrogen atom to which is bonded an alkyl group having ten or more carbon atoms. It has now been discovered that the number of $CH_2$-groups separating the aforesaid onium-nitrogen atoms is indicative of the efficacy of the germicidal properties and other properties such as cariostatic properties of the quaternary compound. In addition, the substantivity of these unsymmetrical quaternaries decreases as the concentration of methanol decreases in aqueous acid containing methanol in proportions varying from zero to fifty-five percent as will be discussed below with regard to chromatography tests.

The novel poly-onium nitrogen compounds of the present invention can be represented by the formula

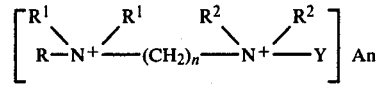

wherein R is a substantially straight chain alkyl group having ten to eighteen carbon atoms; Y is selected from the group consisting of $-CH_2C_6H_{[5-(m+p)]}R_m^3X_p$ and

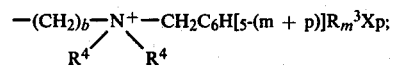

n is an integer 2 to 18; $R^1$, $R^2$, $R^3$ and $R^4$ are lower alkyls having 1 to 3 carbon atoms; b is an integer 2 to 12; X is selected from the group consisting of chlorine, bromine and iodine; m is 0 to 3; p is 0 to 3; m+p is 0 to 3; An is a compatible anion, including halide, such as Cl, Br, or alkyl or phenyl sulfonate, such as $CH_3SO_3-$, $C_2H_5SO_3-$, p-$CH_3C_6H_4SO_3-$, etc. in sufficient number to satisfy the positive valence of the remainder of the compound, that is, 2 or 3. The An groups may be the same or different.

Illustrative of the effect of the value of n in the formula set forth hereinbefore are the following data obtained in anti-microbial tests employing the following organisms:

| Organism No. | |
|---|---|
| 1 | *Staphyloccus aureus* (gram positive bacteria) |
| 2 | *Corynebacterium acnes* (gram positive bacteria) |
| 3 | *Bacillus subtilis* (gram positive bacteria) |
| 4 | *Escherichia coli* (gram negative bacteria) |
| 5 | *Pseudomonas aeruginosa* (gram negative bacteria) |
| 6 | *Candida albicans* (fungus) |
| 7 | *Trichlophyton mentagrophytes* (fungus) |
| 8 | *Aspergillus niger* (fungus) |
| 9 | *Streptococcus mitis* (S-3) (gram positive bacteria) |

The serial dilution test to determine the minimal inhibitory concentration in $\mu g/ml$, i.e., $1 \times 10^{-3}$ mg/ml, has been used to illustrate this important characteristic of these novel poly-onium quaternary ammonium type materials. Two materials of this type, A and B, were used and the chain length (n) varied from 3 to 10 ($CH_2$) groups.

Compound A

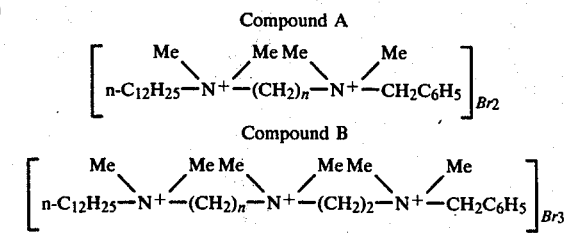

Compound B $$\left[ \begin{array}{c} Me \diagdown \diagup MeMe \diagdown \diagup MeMe \diagdown \diagup Me \\ n\text{-}C_{12}H_{25}-N^+-(CH_2)_n-N^+-(CH_2)_2-N^+-CH_2C_6H_5 \end{array} \right]_{Br_3}$$

In the above compounds, A and B as well as in structural formulae set forth hereinafter, Me indicates a methyl group.

| | Compound A | | | | | | | |
|---|---|---|---|---|---|---|---|---|
| Organism No. | 1 | 2 | 3 | 4 | 5 | 6 | 7 | 8 |
| n | $\mu g/ml$ | $\mu g/ml$ | $\mu g/ml$ | $\mu g/ml$ | $\mu g/ml$ | $\mu g/ml$ | $\mu g/ml$ | $\mu g/ml$ |

| | | | -continued | | | | | |
|---|---|---|---|---|---|---|---|---|
| 3 | 25 | 2.5 | 25 | >100 | >100 | 12.5 | 125 | 1000 |
| 4 | 50 | >100 | 12.5 | 100 | >100 | 25 | >1000 | 500 |
| 6 | 12.5 | 0.78 | 6.25 | 25 | 250 | 1.56 | >7.8 | 250 |
| 8 | 1.56 | <0.2 | 6.25 | 3.12 | 1000 | 1.56 | <7.8 | 31.2 |
| 10 | 0.78 | 0.025 | 1.56 | 12.5 | >100 | 0.78 | 7.8 | 31.3 |
| | | | Compound B | | | | | |
| 4 | 50 | 3.13 | 3.13 | 100 | >100 | 25 | 125 | 1000 |
| 10 | 1.56 | 0.78 | 0.78 | 6.25 | 15.6 | 0.78 | <7.8 | 125 |

Compounds having values of n, ranging from low to high, are effective antimicrobial agents. Generally, the compounds of greater effectiveness have higher values of n. Similar results may be observed when the methyl groups are replaced with ethyl and/or propyl groups.

The effect of a single nuclear substituent, such as a halogen substituent in the benzyl ring is clearly shown by the following comparative results using the serial dilution test and reporting the minimal inhibitory concentration in $\mu g/ml$, that is, $1 \times 10^{-4}$ mg/ml on compounds in which the chain length (n) was 4:

| | Compound A v. Compound $A_{hal}$ | | | | | | | |
|---|---|---|---|---|---|---|---|---|
| | A $[n\text{-}C_{12}H_{25}N^+Me_2(CH_2)_4N^{+Me_2}CH_2C_6H_5]_{Br2}$ | | | | | | | |
| | $A_{hal}$ $[n\text{-}C_{12}H_{25}N^+Me_2(CH_2)_4N^+Me_2CH_2C_6H_4p\text{-}Cl]_{Br2}$ | | | | | | | |
| Organism No. | 1 | 2 | 3 | 4 | 5 | 6 | 7 | 8 |
| | $\mu g/ml$ | $\mu g/ml$ | $\mu g/ml$ | $\mu g/ml$ | $\mu g/ml$ | $\mu g/ml$ | $\mu g/ml$ | $\mu g/ml$ |
| A | 50 | >100 | 12.5 | 100 | >100 | 25 | >1000 | 500 |
| $A_{hal}$ | 6.25 | 0.78 | 6.25 | 25 | 100 | 12.5 | 31.3 | 125 |
| | Compound B v. Compound $B_{hal}$ | | | | | | | |
| | B $[n\text{-}C_{12}H_{25}N^+Me_2(CH_2)_4N^+Me_2(CH_2)_2N^{+Me_2}CH_2C_6H_5]_{Br3}$ | | | | | | | |
| | $B_{hal}$ $[n\text{-}C_{12}H_{25}N^+Me_2(CH_2)_4N^+Me_2(CH_2)_2N^+Me_2CH_2C_6H_4p\text{-}Cl]_{Br2Cl}$ | | | | | | | |
| Organism No. | 1 | 2 | 3 | 4 | 5 | 6 | 7 | 8 |
| | $\mu g/ml$ | $\mu g/ml$ | $\mu g/ml$ | $\mu g/ml$ | $\mu g/ml$ | $\mu g/ml$ | g/ml | g/ml |
| B | 50 | 3.13 | 3.13 | 100 | >100 | 25 | 125 | 1000 |
| $B_{hal}$ | 12.5 | 6.25 | 0.78 | 25 | 100 | 25 | 15.6 | 250 |

Generally speaking the presence of a nuclear substituent such as a halogen substituent in the benzyl ring increases the antimicrobial effectiveness of compounds of the invention. In addition to or in place of the halogen substituent, alkyl substituent, such as methyl, ethyl or propyl, may be present in the benzyl ring.

The following compounds were also tested against the organisms described above and the inhibitory concentration indicated results below were obtained:

| | Compound $C_{hal}$ | | | | | | | | |
|---|---|---|---|---|---|---|---|---|---|
| | $[n\text{-}C_{12}H_{25}N^+Me_2(CH_2)_{10}N^+Me_2CH_2C_6H_4p\text{-}Cl]_{Br2}$ | | | | | | | | |
| | Compound $D_{hal}$ | | | | | | | | |
| | $[n\text{-}C_{14}H_{29}N^+Me_2(CH_2)_{10}N^+Me_2CH_2C_6H_4p\text{-}Cl]_{Br2}$ | | | | | | | | |
| Organism No. | 1 | 2 | 3 | 4 | 5 | 6 | 7 | 8 | 9 |
| | $\mu g/ml$ | $\mu g/ml$ | $\mu g/ml$ | $\mu g/ml$ | $\mu g/ml$ | $\mu g/ml$ | $\mu g/ml$ | $\mu g/ml$ | $\mu g/ml$ |
| $C_{hal}$ | 0.78 | 3.12 | 0.39 | 1.56 | 62.5 | 0.78 | 31.2 | 250 | 3.12 |
| $D_{hal}$ | 0.39 | 3.12 | 0.19 | 0.78 | 31.2 | 0.78 | 1.9 | 62.5 | 0.39 |

Similar results may be obtained when the dodecyl and tetradecyl groups of Compounds $C_{hal}$ and $D_{hal}$ are replaced by shorter substantially straight chain alkyl groups such as n-decyl or n-undecyl, an intermediate alkyl group such as n-tridecyl and longer alkyl groups such as n-pentadecyl, n-hexadecyl, n-heptadecyl and n-octadecyl.

In addition to the antimicrobial effectiveness of compounds of the invention, compounds of the invention are also effective in reducing formation of caries in mammals as demonstrated below:

Caries-susceptible hamsters bred either from the Keyes strain or the NIDR (National Institute for Dental Research) strain in groups of 15 males and 15 females per control group and per each test group were fed ad lib a Mitchell cariogenic diet and received constant deionized water. Each day each hamster's teeth were swabbed 30 seconds by cotton tipped swabs, the control group with water and each test group with its test solution. After 6 weeks of swabbing the animals were sacrificed, and the defleshed heads were scored by a modified version of the Keyes scoring method. Mean averages and percentage changes from the control group were determined and tested statistically to determine the significance.

The compounds were administered in 1% by weight solutions.

| | Results - Hamster Caries Test | |
|---|---|---|
| | Caries Reduction % | |
| Compound | Males | Females |
| $[n\text{-}C_{12}H_{25}N^+(CH_3)_2(CH_2)_{10}N^+(CH_3)_2CH_2C_6H_4p\text{-}Cl]_{Br2}$ | −75.4 | −77.9 |

-continued

Results - Hamster Caries Test

| Compound | Caries Reduction % | |
|---|---|---|
| | Males | Females |
| $[n\text{-}C_{14}H_{29}N^+(CH_3)_2(CH_2)_{10}N^+(CH_3)_2CH_2C_6H_4p\text{-}Cl]_{Br_2}$ | −51.7 | −61.2 |

The results above indicate the significant effectiveness of the compounds of the invention in reducing caries formation.

When used against bacteria and fungi, compounds of the instant invention may be applied directly to the surface to be protected or may be used in a pharmaceutical carrier. Typically an effective amount, e.g. 0.1 to about 10% by weight of the quaternary is included in an inert liquid carrier such as water and a dispersing or surface active agent. Alternatively, an effective amount, e.g. 0.1 to about 10% by weight may be incorporated into a solid carrier which may be inert, such as talc, clay, diatomaceous earth, flour, etc.

When compounds of the invention are used in compositions which reduce formation of carier they are typically incorporated in oral preparations in effective amounts up to about 5% by weight, preferably 0.1% and most preferably 0.25–0.5% by weight of the oral preparation. Typically, the oral preparation is a dentifrice such as a dental cream, tablet or powder, containing as a vehicle about 20–95% by weight of a dentally acceptable water-insoluble polishing material, preferably including water-insoluble phosphates such as dicalcium phosphate, tricalcium phosphate, insoluble sodium metaphosphate and calcium pyrophosphate. The dentifrice may also include water, binders such as glycerine, sorbitol, propylene glycol and polyethylene glycol 400, gelling agents such as Irish moss and sodium carboxymethyl cellulose, additional antibacterial agents, coloring or whitening agents, preservatives, silicones, chlorophyll compounds, additional ammoniated materials, flavoring or sweetening materials and dentally beneficial compounds which provide fluorine-containing ion such as sodium fluoride, stannous fluoride and sodium monofluorophosphate.

The oral preparation may also be a liquid such as a mouth rinse which typically contains 20–99% by weight of an aqueous alcohol vehicle, the alcohol being a cosmetically acceptable and nontoxic alcohol such as ethanol or isopropyl alcohol and being present in amount of about 5–30% by weight of the oral preparation.

Such oral preparations are typically applied by brushing the teeth or rinsing the oral cavity for 30–90 seconds at least once daily. Typical oral preparations including a compound of the instant invention are set forth as follows:

| Dental Cream | | Mouth Wash | |
|---|---|---|---|
| Component | Parts By Weight | Component | Parts By Weight |
| Quaternary $D_{hal}$ | 0.5 | Quaternary $C_{hal}$ | 0.25 |
| Sodium Benzoate | 0.15 | Ethyl Alcohol | 14.782 |
| Saccharine | 0.2 | Flavor | 0.318 |
| Insoluble Sodium Metaphosphate | 42.1 | Glycerine | 10.000 |
| Dicalcium Phosphate Dihydrate | 5.0 | Deionized Water | 74.1 |
| Titanium Dioxide | 0.4 | Color (1% Solution) | 0.55 |
| Gum Tragacanth | 1.4 | | |
| Oil of Wintergreen | 1.0 | | |
| Color | 0.03 | | |
| Water | 22.12 | | |
| Glycerine (99.3%) | 27.10 | | |

The relative substantivity of the novel poly-onium quaternary ammonium compounds of the present invention compared to mono-onium quaternaries and symmetrical bis and tetrakis quaternaries was studied on two substrates, viz. cellulose and polyamide by a chromatographic technique. $R_F'$ and $R_F$ values were determined in aqueous acid containing proportions of methanol varying from 0 to 55 percent. Compared to the other classes of quaternaries the poly-onium quaternary ammonium compounds of the present invention show a decrease in substantivity as the concentration of methanol in the solvent decreases. These substantivity tests were carried out as follows:

Paper Chromatography

Whatman No. 1 paper was spotted with 2 $\mu l$ aliquots of 1% solutions of the quaternaries. After overnight equilibration in a tank containing the solvent to be used, the chromatograms were developed in the descending manner to a distance of about 14 inches at room temperature. After drying, the papers were dipped in a dilute ammoniacal solution of bromophenol blue and then held under running water until all removable dye had been washed away. The presence of quaternary is revealed by a bright blue spot (soluble in organic solvents, but insoluble in water) against a white background; the color tends to fade with time, but can usually be restored by retreatment with bromophenol blue. Acid was necessary in the developing solvent to diminish streaking, but the relative positions of various quaternaries was not different whether the solvent was neutral, acidic, or basic. The $R_F'$ values were found to vary somewhat with the amount of quaternary applied to the paper; hence the solutions were carefully prepared to the same concentration, and the spotting was done with micro pipettes to insure that equal quantities of all quaternaries were being compared. In addition, replicates were run on different days and the results averaged to obtain the values given in Tables I and II below.

Polyamide Thin Layer Chromatography

8 × 8 inch glass plates were coated in Kensco variable thickness applicator with approximately 250 micron layers of a slurry of Polyamide Woelm for TLC in chloroform-methanol. Uniform adherent layers were obtained on drying in a moderately humid atmosphere. These plates were spotted with 8–10 $\mu l$ aliquots of 1% solutions of quaternaries and developed in the ascending manner. After drying, visualization was accomplished by spraying with a fine mist of a 0.1% solution of Direct Fast Rubine WS dye (Ciba), whereupon the quaternaries were seen as pink spots on a red background. Streaking was not a problem on these plates even when no acid was used in the solvent, but in the results reported in Table III, below, an acidic system was used.

Although these substrates are different in that one is a carbohydrate and the other an amide, the results were found to correlate very closely as shown in FIG. 1 where for each quaternary the $R_F'$ value obtained on paper is plotted against its $R_F$ value on polyamide. The tendency of the points to fall on a straight line is evidence that the binding to paper is similar in nature to the binding to polyamide, and hence one can feel confident about extrapolating the results to protein and the specific types of surfaces present in the body. Most of the work was done on paper because of the greater convenience and the more sensitive detection system. Thus, the mono-quaternaries, $RNMe_2(CH_2)xBr$, where R is n-dodecyl and x is 2, 3, 4, 8 and 10, are represented by open circles; the symmetrical bisquaternaries, $RNMe_2(CH)_xNMe_2R$, where R is n-dodecyl and x is 6, 8 and 10, are represented by open squares; the unsymmetrical bisquaternaries and trisquaternaries are represented by solid triangles, and the control, $RNMe_2CH_2\phi$, wherein R is n-dodecyl, by a solid circle.

Large differences in mobility were observed among the quaternaries as seen in the tabulation of results in the various solvents. It is particularly interesting to plot the results in the form of relative mobilities; relative, that is, to one quaternary chosen as a standard, namely n-dodecyldimethylbenzylammonium chloride. The ratio of the $R_F$ value of any specific quaternary to the $R_F$ value of the standard quaternary under the same conditions will be referred to hereafter as $R_Q$, and the ratio of $R_F'$ values as $R_Q'$, where $R_F$ and $R_F'$ have the meanings ascribed to them in the literature. It was convenient to use $R_F$ and $R_Q$ for the polyamide chromatograms because the quaternaries traveled in small regularly shaped spots, whereas $R_F'$ and $R_Q'$ were more appropriate values to measure on paper where the spots tended to be elongated and to have no easily located center of maximum density.

The bromoalkyl quaternaries show a large variation with molecular weight in $R_Q'$ values plotted against methanol concentration in the developing solvent (FIG. 2). However, the series of symmetrical bisquaternaries and unsymmetrical bisquaternaries (FIG. 3) show little variation with molecular weight within each group, but display a striking difference between the two types. Although fewer examples of the unsymmetrical trisquaternaries are available they display the same behavior as the unsymmetrical bisquaternaries. The two quaternaries containing the p-chlorobenzyl group showed slightly greater binding than their analogs.

These data are from paper chromatography; although only two different solvent compositions were used for chromatography on polyamide, the slopes of the lines connecting these two points have the same direction as the curves obtained with paper, which is further evidence for the similarity of the binding for the two media.

$$R_F = \frac{\text{Movement of spot}}{\text{Movement of advancing front of liquid}}$$

$$R_F' = \frac{\text{Movement of leading edge of spot}}{\text{Movement of advancing front of liquid}}$$

In all cases in Tables I, II and III, R represents n-dodecyl.

Table I

| | $R_F$ in the System: Cellulose - Acidic Aqueous Methanol | | | | | |
|---|---|---|---|---|---|---|
| | Vol. % MeOH | | | | | |
| Structure | 0 | 10 | 20 | 25 | 40 | 55 |
| $RNMe_2(CH_2)_xBr$ | | | | | | |
| x = 2 | 0.43 | 0.50 | | 0.68 | 0.86 | 0.93 |
| 3 | .32 | .42 | | .61 | .83 | .93 |
| 4 | .27 | .36 | | .55 | .82 | .93 |
| 6 | .15 | .22 | | .39 | .74 | .93 |
| 8 | .07 | .10 | | .19 | .57 | .88 |
| 10 | 0 | .08 | 0.09 | .12 | .37 | .76 |
| $RNMe_2(CH_2)_3Cl$ | .37 | .46 | | .65 | .85 | .94 |
| $RNMe_2(CH_2)_xNMe_2R$ | | | | | | |
| x = 3 | .10 | .12 | .13 | .15 | .33 | .71 |
| 4 | .12 | .14 | .13 | .15 | .38 | .76 |
| 6 | .14 | .15 | .15 | .17 | .45 | .82 |
| 8 | .17 | .16 | .16 | .18 | .45 | .82 |
| 10 | .17 | .16 | .17 | .18 | .46 | .85 |
| $RNMe_2(CH_2)_xNMe_2CH_2\phi$ | | | | | | |
| x = 2 | .57 | .64 | | .76 | .90 | .94 |
| 3 | .56 | .66 | | .76 | .88 | .95 |
| 4 | .60 | .66 | | .78 | .91 | .95 |
| 6 | .56 | .66 | | .79 | .91 | .95 |
| 8 | .47 | .58 | | .76 | .91 | .94 |
| 10 | .45 | .54 | | .72 | .88 | .95 |
| $RNMe_2CH_2\phi$ | .31 | .39 | .53 | .60 | .84 | .94 |
| $RNMe_2(CH_2)_4NMe_2CH_2\phi$ | .60 | .66 | | .78 | .91 | .95 |
| $RNMe_2(CH_2)_4NMe_2(CH_2)_2NMe_2CH_2\phi$ | .62 | .70 | | .80 | .90 | .92 |
| $RNMe_2(CH_2)_4NMe_2CH_2\langle\bigcirc\rangle Cl$ | .43 | .51 | | .67 | .87 | .93 |
| $RNMe_2(CH_2)_4NMe_2(CH_2)_2NMe_2CH_2\langle\bigcirc\rangle Cl$ | .54 | .60 | | .72 | .89 | .92 |
| $RNMe_2(CH_2)_{10}NMe_2CH_2\phi$ | .45 | .54 | | .72 | .91 | .95 |
| $RNMe_2(CH_2)_{10}NMe_2(CH_2)_2NMe_2CH_2\phi$ | .51 | .62 | | .77 | .90 | .94 |
| $RNMe_2CH_2CH_2NMe_2$ | .69 | .73 | | .82 | .91 | .92 |
| $RNMe_2(CH_2)_4NMe_2CH_2CH_2NMe_2$ | .72 | .78 | | .85 | .92 | .93 |

Table I-continued
R$_F$ in the System: Cellulose - Acidic Aqueous Methanol

| Structure | Vol. % MeOH | | | | | |
|---|---|---|---|---|---|---|
| | 0 | 10 | 20 | 25 | 40 | 55 |
| RNMe$_2$(CH$_2$)$_{10}$NMe$_2$CH$_2$CH$_2$NMe$_2$ | .60 | .69 | | .80 | .91 | .96 |

Table II
R$_Q$ in the System: Cellulose - Acidic Aqueous Methanol

| Structure | Vol. % MeOH | | | | | |
|---|---|---|---|---|---|---|
| | 0 | 10 | 20 | 25 | 40 | 55 |
| RNMe$_2$(CH$_2$)$_x$Br | | | | | | |
| x = 2 | 1.41 | 1.29 | | 1.10 | 1.02 | 0.99 |
| 3 | 1.01 | 1.10 | | 1.00 | 1.00 | .99 |
| 4 | .90 | .93 | | .89 | .98 | .99 |
| 6 | .50 | .55 | | .64 | .89 | .99 |
| 8 | .21 | .22 | | .32 | .67 | .94 |
| 10 | 0 | .19 | 0.18 | .20 | .43 | .81 |
| RNMe$_2$(CH$_2$)$_3$Cl | 1.21 | 1.18 | | 1.05 | 1.02 | 1.00 |
| RNMe$_2$(CH$_2$)$_x$NMe$_2$R | | | | | | |
| x = 3 | .33 | .31 | .25 | .24 | .37 | .76 |
| 4 | .41 | .36 | .25 | .24 | .43 | .82 |
| 6 | .44 | .38 | .29 | .29 | .50 | .87 |
| 8 | .54 | .40 | .30 | .30 | .51 | .88 |
| 10 | .53 | .40 | .32 | .31 | .50 | .90 |
| RNMe$_2$(CH$_2$)$_x$NMe$_2$CH$_2\phi$ | | | | | | |
| x = 2 | 1.84 | 1.65 | | 1.28 | 1.07 | .99 |
| 3 | 1.89 | 1.70 | | 1.25 | 1.10 | 1.00 |
| 4 | 1.96 | 1.77 | | 1.33 | 1.11 | 1.01 |
| 6 | 1.86 | 1.75 | | 1.34 | 1.12 | 1.02 |
| 8 | 1.52 | 1.52 | | 1.28 | 1.08 | 1.02 |
| 10 | 1.50 | 1.45 | | 1.23 | 1.10 | 1.02 |
| RNMe$_2$CH$_2\phi$ | 1.00 | 1.00 | | 1.00 | 1.00 | 1.00 |
| RNMe$_2$(CH$_2$)$_4$NMe$_2$CH$_2\phi$ | 1.96 | 1.77 | | 1.33 | 1.11 | 1.01 |
| RNMe$_2$(CH$_2$)$_4$NMe$_2$(CH$_2$)$_2$NMe$_2$CH$_2\phi$ | 2.07 | 1.90 | | 1.34 | 1.11 | .99 |
| RNMe$_2$(CH$_2$)$_4$NMe$_2$CH$_2$Cl | 1.41 | 1.38 | | 1.14 | 1.05 | .99 |
| RNMe$_2$(CH$_2$)$_4$NMe$_2$(CH$_2$)$_2$NMe$_2$CH$_2$Cl | 1.77 | 1.54 | | 1.24 | 1.08 | .96 |
| RNMe$_2$(CH$_2$)$_{10}$NMe$_2$CH$_2\phi$ | 1.50 | 1.45 | | 1.23 | 1.10 | 1.02 |
| RNMe$_2$(CH$_2$)$_{10}$NMe$_2$(CH$_2$)$_2$NMe$_2$CH$_2\phi$ | 1.68 | 1.66 | | 1.27 | 1.11 | 1.00 |
| RNMe$_2$CH$_2$CH$_2$NMe$_2$ | 2.03 | 1.95 | | 1.37 | 1.10 | .99 |
| RNMe$_2$(CH$_2$)$_4$NMe$_2$CH$_2$CH$_2$NMe$_2$ | 2.40 | 2.11 | | 1.36 | 1.11 | .99 |
| RNMe$_2$(CH$_2$)$_{10}$NMe$_2$CH$_2$CH$_2$NMe$_2$ | 1.99 | 1.85 | | 1.34 | 1.11 | 1.00 |

Table III
R$_F$ and R$_Q$ in the System: Polyamide - Aqueous Methanol

| Structure | 40% MeOH | | 52.5% MeOH | |
|---|---|---|---|---|
| | R$_F$ | R$_Q$ | R$_F$ | R$_Q$ |
| RNMe$_2$(CH$_2$)$_x$Br | | | | |
| x = 2 | 0.57 | 1.34 | 0.77 | 1.07 |
| 3 | .54 | 1.09 | .77 | 1.08 |
| 4 | .40 | .90 | .72 | 1.01 |
| 8 | .19 | .45 | .49 | .74 |
| 10 | .07 | .16 | .35 | .54 |
| RNMe$_2$(CH$_2$)$_3$Cl | .53 | 1.24 | .77 | 1.08 |
| RNMe$_2$(CH$_2$)$_x$NMe$_2$R | | | | |
| x = 3 | | | .53 | .75 |
| 4 | | | .41 | .61 |
| 6 | .22 | .53 | .54 | .78 |
| 8 | .22 | .55 | .54 | .80 |
| 10 | .24 | .52 | .38 | .58 |
| RNMe$_2$(CH$_2$)$_x$NMe$_2$CH$_2\phi$ | | | | |
| x = 3 | .70 | 1.64 | .88 | 1.24 |
| 4 | .74 | 1.60 | .84 | 1.29 |
| 6 | .69 | 1.67 | .88 | 1.27 |
| 10 | .68 | 1.48 | .84 | 1.21 |
| RNMe$_2$CH$_2\phi$ | .44 | 1.00 | .69 | 1.00 |
| RNMe$_2$(CH$_2$)$_4$NMe$_2$CH$_2\phi$ | .74 | 1.60 | .84 | 1.29 |
| RNMe$_2$(CH$_2$)$_4$NMe$_2$(CH$_2$)$_2$NMe$_2$CH$_2\phi$ | .78 | 1.76 | .85 | 1.22 |

Table III-continued

| | R$_F$ and R$_Q$ in the System: Polyamide - Aqueous Methanol | | | |
|---|---|---|---|---|
| | 40% MeOH | | 52.5% MeOH | |
| Structure | R$_F$ | R$_Q$ | R$_F$ | R$_Q$ |
| RNMe$_2$(CH$_2$)$_4$NMe$_2$CH$_2$–C$_6$H$_5$ Cl | .59 | 1.40 | .88 | 1.26 |
| RNMe$_2$(CH$_2$)$_4$NMe$_2$(CH$_2$)$_2$NMe$_2$CH$_2$–C$_6$H$_5$ Cl | .70 | 1.66 | .89 | 1.28 |
| RNMe$_2$(CH$_2$)$_{10}$NMe$_2$CH$_2$φ | .68 | 1.48 | .84 | 1.21 |
| RNMe$_2$(CH$_2$)$_{10}$NMe$_2$(CH$_2$)$_2$NMe$_2$CH$_2$φ | .73 | 1.66 | .86 | 1.24 |
| RNMe$_2$CH$_2$CH$_2$NMe$_2$ | .76 | 1.65 | | |
| RNMe$_2$(CH$_2$)$_4$NMe$_2$CH$_2$CH$_2$NMe$_2$ | .83 | 1.85 | .93 | 1.31 |
| RNMe$_2$(CH$_2$)$_{10}$NMe$_2$CH$_2$CH$_2$NMe$_2$ | .84 | 1.90 | .88 | 1.26 |

From the comparative data showing the relative substantivity of the novel poly-onium quaternaries of the present invention and prior art mono-onium, and symmetrical bisquaternaries of the prior art those skilled in the art will recognize that the enhanced desorbability of these compounds makes them more readily available for disinfecting purposes than the less readily desorbed prior art quaternaries.

Those skilled in the art will also observe that in the unsymmetrical compounds of the present invention the increased spacing between the terminal onium-nitrogen to which the oliophyllic alkyl group is attached and the next onium-nitrogen increases the anti-microbial activity of these compounds whereas in the symmetrical bisquaternaries listed in Tables I-III, the activity is essentially unchanged.

The novel poly-onium quaternary ammonium compounds of the present invention can be prepared by the methods of organic chemistry known by those skilled in the art. Presently, it is preferred to obtain these novel poly-onium compounds by first preparing a quaternary ammonium compound by the reaction of a tertiary amine with an alkylene dihalide under suitable reaction conditions. The reaction can be illustrated by the following equation:

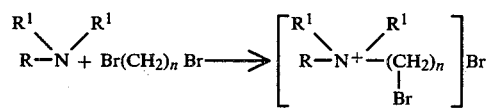

The trialkyl(ω-haloalkyl)ammonium bromide is then reacted with (1) dialkyl benzyl amine or (2) dialkyl halobenzylamine or (3) alkylated dialkylbenzylamine or (4) dialkyl polyhalobenzylamine as can be represented by the following equation:

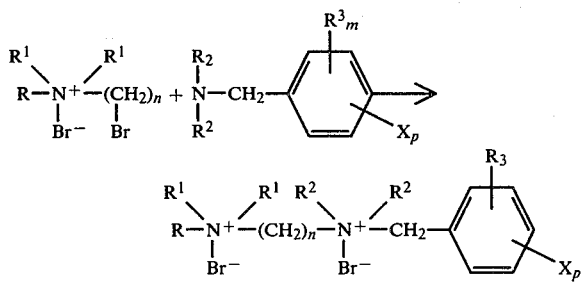

(The symbols R, R$^1$, R$^2$, R$^3$, X, n, m, and p in the foregoing equations have the same significance as hereinbefore initially defined).

The unsymmetrical or asymmetrical bisquaternary amines in which R is n-C$_{12}$H$_{25}$; n is 3, 4, 6, 8, and 10; m is 0, p is 1 and X is chlorine, have been prepared in accordance with the method set forth in Example 1.

EXAMPLE 1 n-dodecyldimethylamine was reacted with a large excess of Br(CH$_2$)$_n$Br in water at 25°-40° C. to form n-dodecyldimethyl(omega-bromoalkyl)ammonium bromide. This quaternary ammonium bromide was refluxed in water with a twofold excess of dimethyl-p-chlorobenzylamine. The products, the bisquaternary ammonium bromides in which n is 3, 4, 6 and 8, were recrystallized from acetone. The unsymmetrical or asymmetrical bis-quaternaries wherein R is n-C$_{12}$H$_{25}$; R$^1$ is CH$_3$; R$^2$ is CH$_3$; n is 3, 4, 6, 8 and 10; m is 0; and p is 0 were observed to have the following characteristics closely akin to the calculated characteristics:

| n = 3 | | |
|---|---|---|
| | Br - 29.03% Cal. | N - 5.09% Cal. |
| | Br - 28.75% Obs. | N - 5.00% Obs. |
| n = 4 | | |
| | Br - 28.32% Cal. | N - 4.96% Cal. |
| | Br - 28.00% Obs. | N - 4.84% Obs. |
| n = 6 | | |
| | Br - 26.97% Cal. | |
| | Br - 27.17% Obs. | |
| n = 8 | | |
| | Br - 25.75% Cal. | |
| | Br - 25.16% Obs. | |
| n = 10 | | |
| | Br - 24.64% Cal. | N - 4.32% Cal. |
| | Br - 23.68% Obs. | N - 3.96% Obs. |

These compounds are further characterized by the chromatographic properties hereinbefore described.

Compounds including 1-p-chlorophenyl-2,2,13,13-tetramethyl-2,13-diazonia heptacosane dibromide [n-C$_{14}$H$_{29}$N$^+$(Me)$_2$(CH$_2$)$_{10}$N$^+$(Me)$_2$CH$_2$C$_6$H$_4$-p-Cl]Br$_2$ have been similarly prepared using tetradecyldimethyl amine as a starting reactant. Alternatively, the dimethyl-p-chlorobenzylamine can be reacted with alkylene dibromide [Br(CH$_2$)$_n$Br] and the reaction product reacted with tetradecyldimethyl amine.

The poly-onium quaternary ammonium compounds represented by the formula $$\left[ \begin{array}{c} R^1 \diagdown \diagup R^1 \quad R^2 \diagdown \diagup R^2 \\ R-N^+-(CH_2)_n-N^+-Y \end{array} \right] [Hal]_3$$

where Y is $$-(CH_2)_b-\overset{R^4}{\underset{R^4}{\diagdown \diagup}}N^+-CH_2-\underset{X_p}{\bigcirc}^{R_m^3},$$

b is 2 or 3, n is 3 to 10 and is greater than b, m is 0 to 3, p is 0 to 3, m+p is 0 to 3, and Hal is a Halide while R, $R^1$, $R^2$, $R^3$, $R^4$ and X have the same significance as hereinbefore are prepared from the backbone, trialkylhaloalkylhalide, $$\left[ \begin{array}{c} R^1 \diagdown \diagup R^1 \\ R-N^+-(CH_2)_n \\ | \\ Hal \end{array} \right] Hal$$

That is to say the trialkylhaloalkylhalide is reacted with N,N,N',N'-tetraalkyl alkylene diamine, e.g., N,N,N',N'-tetramethylethylenediamine to produce poly-onium halide as indicated by the following equation to obtain $$\overset{R^1}{\underset{}{\diagdown}}\overset{}{\underset{R^1}{\diagup}} \quad \overset{R^2}{\underset{}{\diagdown}}\overset{}{\underset{R^2}{\diagup}} \overset{R^4}{\underset{}{\diagdown}}\overset{}{\underset{R^4}{\diagup}}$$
$$R-N^+-(CH_2)_nHal^- + N-(CH_2)_b-N \longrightarrow$$
$$\quad | \\ Hal$$

$$\overset{R^1}{\underset{}{\diagdown}}\overset{}{\underset{R^1}{\diagup}} \overset{R^2}{\underset{}{\diagdown}}\overset{}{\underset{R^2}{\diagup}} \overset{R^4}{\underset{}{\diagdown}}\overset{}{\underset{R^4}{\diagup}}$$
$$R-N^+-(CH_2)_n-N^+-(CH_2)_b-N$$
$$\quad | \qquad\qquad\qquad | \\ Hal^- \qquad\qquad Hal^-$$

The poly-onium halide is then reacted with a benzyl halide to produce the poly-onium quaternary compound represented by the formula $$\left[ \begin{array}{c} R^1 \diagdown \diagup R^1 \; R^2 \diagdown \diagup R^2 \; R^4 \diagdown \diagup R^4 \qquad R_m^3 \\ R-N^+-(CH_2)_nN^+-(CH_2)_b-N^+-CH_2-\underset{X_p}{\bigcirc} \end{array} \right] [Hal]_3$$

where R, $R^1$, $R^2$, $R^3$, X and Hal, n, b, m, and p have the same significance as hereinbefore indicated in this paragraph.

Illustrative of the preparation of these latter polyonium quaternary ammonium compounds is the production of the quaternaries represented by the formula $$\left[ \begin{array}{c} Me \diagdown \diagup Me \; Me \diagdown \diagup Me \; Me \diagdown \diagup Me \\ C_{12}H_{25}N^+-(CH_2)_n-N^+-(CH_2)_2-N^+-CH_2-\bigcirc \end{array} \right] An_3$$

where n is 4 and 10 and An has the same significance as hereinbefore; and the quaternary represented by the formula $$\left[ \begin{array}{c} Me \diagdown \diagup Me \; Me \diagdown \diagup Me \; Me \diagdown \diagup Me \\ C_{12}H_{25}N^+-(CH_2)_4-N^+-(CH_2)_2-N^+-CH_2-\bigcirc Cl \end{array} \right] An_3$$

wherein An has the significance as hereinbefore. These preparations are set forth in Example 2.

EXAMPLE 2 n-Dodecyldimethyl-omega-bromo-alkyl halide was reacted with N,N,N',N'-tetramethylethylenediamine at 25° C. in the molal ratio of 1:8. The resulting bis-quaternary was recrystallized from acetone-chloroform. The recrystallized bis-quaternary was reacted separately with benzyl bromide and chloro-benzyl bromide at 25° C. to obtain the poly-onium quaternary ammonium bromide. The poly-onium quaternary ammonium bromides thus prepared have the following characteristics:

| [n-$C_{12}H_{25}N^+Me_2(CH_2)_4N^+Me_2(CH_2)_2N^+Me_2CH_2C_6H_5$]$_{Br_3}$·½$H_2O$ | | |
|---|---|---|
| | Cal. | Obs. |
| Bromine | 33.04% | 33.05% |
| Melting Point | 151–155° C. | |
| Nitrogen | 5.79% | 5.86% |
| [n-$C_{12}H_{25}N^+Me_2(CH_2)_{10}N^+Me_2(CH_2)_2N^+Me_2CH_2C_6H_5$]$_{Br_3}$ | | |
| | Cal. | Obs. |
| Bromine | 29.94% | 28.63% |
| Nitrogen | 5.25% | 4.93% |
| [n-$C_{12}H_{25}N^+Me_2(CH_2)_4N^+Me_2(CH_2)_2N^+Me_2CH_2C_6H_4$ Cl]$_{Br_2Cl}$ | | |
| | Cal. | Obs. |
| Total Halogen | 27.65% | 28.38 |

Although this invention has been described with reference to specific examples, it will be apparent to one skilled in the art that various modifications may be made thereto which fall within its scope.

What is claimed is:

1. Unsymmetrical poly-onium quaternary compound having the structural formula:

$$[R-\overset{R' \diagdown \diagup R'}{N^+}-(CH_2)_n-\overset{R' \diagdown \diagup R'}{N^+}-Y]A_n$$

wherein

R is a straight chain alkyl group having 10 to 18 carbon atoms;

$$Y \text{ is } -(CH_2)_b-\overset{R^4}{\underset{R^4}{\diagdown \diagup}}N^+-CH_2\, C_6\, H_{[5-(m\ p)]}\, R_m^3\, X_p\, ;$$

n is an integer 2 to 18;

$R^1$, $R^2$, $R^3$ and $R^4$ are lower alkyls having 1 to 3 carbon atoms;

b is an integer 2 to 12;

X is selected from the group consisting of chlorine, bromine and iodine;

m is 0 to 3;

p to 0 to 3;

m+p is 0 to 3; and $A_n$ is a compatible anion selected from the group consisting of halide, alkyl sulfonate and phenyl sulfonate.

2. Unsymmetrical poly-onium quaternary ammonium compound as set forth in claim 1 wherein R is n-$C_{12}H_{25}$, and n is an integer 3 to 10.

3. Unsymmetrical poly-onium quaternary ammonium compound as set forth in claim 2 wherein Y is

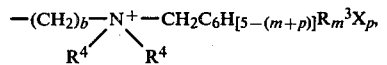

b is 2, m is zero and p is zero.

4. Unsymmetrical poly-onium quaternary ammonium compound as set forth in claim 2 wherein Y is

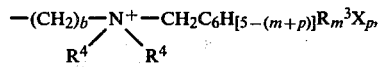

b is 2, m is zero, p is 1 and X is chlorine.

5. Unsymmetrical poly-onium quaternary ammonium compound as set forth in claim 1 wherein $R^1$, $R^2$, $R^3$ and $R^4$ are $CH_3$.

6. Unsymmetrical poly-onium quaternary ammonium compound as set forth in claim 1 wherein R is n-$C_{14}H_{29}$.

7. Unsymmetrical poly-onium quaternary ammonium compound as set forth in claim 6 wherein n is 10.

* * * * *